United States Patent [19]

von Locquenghien et al.

[11] Patent Number: 5,332,830
[45] Date of Patent: Jul. 26, 1994

[54] PREPARATION OF N-HYDROXYAZOLES

[75] Inventors: Klaus H. von Locquenghien, Neuhofen; Wolfgang Hoelderich, Frankenthal; Ulf Baus, Dossenheim; Wolfgang Reuther; Erwin Hahn, both of Heidelberg, all of Fed. Rep. of Germany

[73] Assignee: BASF Aktiengesellschaft, Ludwigshafen, Fed. Rep. of Germany

[21] Appl. No.: 37,910

[22] Filed: Mar. 26, 1993

[30] Foreign Application Priority Data

Apr. 30, 1992 [DE] Fed. Rep. of Germany ....... 4214174

[51] Int. Cl.$^5$ ............... C07D 249/08; C07D 233/56; C07D 231/12
[52] U.S. Cl. ............... 548/262.2; 548/335.1; 548/343.1; 548/373.1
[58] Field of Search ............... 548/262.2, 335.1, 343.1, 548/373.1

[56] References Cited

U.S. PATENT DOCUMENTS

| 3,329,481 | 7/1967 | Young et al. | 23/111 |
|---|---|---|---|
| 4,410,501 | 10/1983 | Taramasso et al. | 423/326 |
| 4,945,166 | 7/1990 | Baus et al. | 548/369 |
| 4,945,167 | 7/1990 | Baus et al. | 548/375 |
| 4,957,937 | 9/1990 | Schuetz et al. | 514/407 |
| 5,049,678 | 9/1991 | Baus et al. | 548/263.2 |
| 5,112,985 | 5/1992 | Baus et al. | 548/337 |

FOREIGN PATENT DOCUMENTS 0311983 4/1989 European Pat. Off. .
0314147 5/1989 European Pat. Off. .
2116974 10/1983 United Kingdom .

Primary Examiner—Patricia L. Morris
Attorney, Agent, or Firm—John H. Shurtleff

[57] ABSTRACT

N-Hydroxyazoles of the general formula I

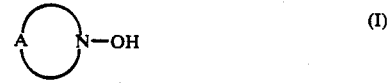

where A is

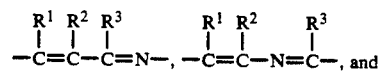

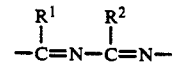

and $R^1$, $R^2$ and $R^3$ are each hydrogen, $C_1$-$C_4$-alkyl or halogen, are prepared by a process in which an azole of the general formula II

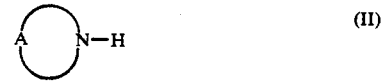

where A, $R^1$, $R^2$ and $R^3$ have the abovementioned meanings, is reacted with hydrogen peroxide or an alkyl peroxide in the presence of a zeolite catalyst at from $-20°$ to $150°$ C. and from 0.1 to 150 bar.

5 Claims, No Drawings

PREPARATION OF N-HYDROXYAZOLES

The present invention relates to a process for the preparation of N-hydroxyazoles, such as N-hydroxypyrazoles, N-hydroxyimidazoles and N-hydroxy-1,2,4-triazoles, from the corresponding azoles with hydrogen peroxide in the presence of zeolites.

DE-A-38 20 739 discloses the oxidation of pyrazole to N-hydroxypyrazole in the homogeneous phase under basic reaction conditions with peroxocarboxylic acids, and DE-A-38 20 738 discloses the corresponding oxidation with diacyl peroxides.

EP-A-420 092 discloses a similar process for the preparation of N-hydroxy-1,2,4-triazole.

The disadvantages in these procedures are the fact that the reaction is carried out in the homogeneous phase and the coupled production of salts and carboxylic acids in amounts larger than the amount of the particular desired product. Furthermore, the reactive material has to meet higher requirements owing to the oxidizing agents used (corrosion). The typical problems of homogeneous catalysis, such as isolation, regeneration and working up of the catalyst, are also likely.

It is an object of the present invention to remedy the abovementioned disadvantages.

We have found that this object is achieved by a novel and improved process for the preparation of N-hydroxyazoles of the general formula I

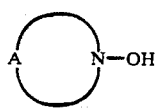
(I)

where A is

and

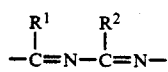

and $R^1$, $R^2$ and $R^3$ are each hydrogen, $C_1$–$C_4$-alkyl or halogen, wherein an azole of the general formula II

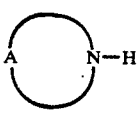
(II)

where A, $R^1$, $R^2$ and $R^3$ have the abovementioned meanings, is reacted with hydrogen peroxide or an alkyl peroxide in the presence of a zeolite catalyst at from −20° to 150° C. and from 0.1 to 150 bar.

The novel process can be carried out as follows:

The zeolite catalyst can be added to the azole II, dissolved in a solvent. The reaction temperature and the reaction pressure can then be set. Hydrogen peroxide or the alkyl peroxide is then added, preferably dropwise.

The reaction temperature is from −20° to 150° C., preferably from 0° to 120° C. in particular from 20° to 80 ° C., and the pressure is from 0.1 to 150, preferably from 0.5 to 80, in particular from 0.8 to 30, bar.

The process can be carried out batchwise in the liquid phase in a stirred apparatus but may also be effected continuously in a trickle-bed reactor or liquid-phase reactor.

The solvents used may be water as well as organic solvents, for example aliphatic alcohols, such as $C_1$-$C_4$-alkanols, e.g. methanol, ethanol, n-propanol, isopropanol, n-butanol, isobutanol, sec-butanol or tert-butanol, ketones, such as $C_2$-$C_8$-ketones, e.g. acetone or methyl ethyl ketone, and other water-miscible substances. The best results have been obtained with the use of methanol, acetone, isopropanol and tert-butanol and mixtures thereof.

The amount of catalyst used is from 0.1 to 200, preferably from 5 to 100, in particular from 10 to 80, % by weight, based on the azole II. After the end of the reaction, the catalyst is separated off, for example by filtration. It can then be used again for further reactions. The reaction solution is worked up by known methods, for example as described in DE-A-38 20 739.

Hydrogen peroxide or an alkyl peroxide serves as an oxidizing agent for the novel process. Hydrogen peroxide may preferably be used in the form of its aqueous solution. Preferably from 10 to 50, in particular from 20 to 35, % strength by weight aqueous hydrogen peroxide solutions are used. It is also possible to use alkyl peroxides, such as $C_1$-$C_8$-alkyl hydroperoxides, e.g. tert-butyl hydroperoxide or cyclohexyl hydroperoxide.

The molar ratio of hydrogen peroxide or of alkyl peroxide to the azole II is as a rule from 0.5:1 to 5:1, preferably from 0.7:1 to 3:1, particularly preferably from 0.9:1 to 1.5:1.

The novel reaction is catalyzed by zeolites.

Zeolites are known to be crystalline aluminosilicates having ordered channel and cage structures whose pore openings are in the range of micropores smaller than 1.2 nm. The network of such zeolites is composed of $SiO_4$ and $AlO_4$ tetrahedra, which are linked via common oxygen bridges.

An overview of the known structures appears, for example, in W. M. Meier and D. H. Olson, Atlas of Zeolite Structure Types, 2nd Edition, Butterworths, London 1987. To compensate for the negative electrovalency due to the incorporation of Al(III) in the Si(IV) silicate framework, the zeolites contain exchangeable cations, in particular cations of sodium, of potassium, of lithium or of cesium, depending on the preparation process. If these cations are exchanged for protons, for example by ion exchange, the corresponding acidic solids having a zeolite structure, i.e. the H form, are obtained.

Zeolites of the pentasil type (MFI structure; G. T. Kokotailo and W. M. Meier, Spec. Publ. Chem. Soc. 33 (1980), 133) are particularly advantageous. The common feature of these is the basic building block comprising a 5-membered ring composed of $SiO_4$ tetrahedra. They possess a high $SiO_2/Al_2O_3$ ratio and pore sizes which are between those of the zeolites of type A and those of type X or Y (cf. Ullmanns Encyklopädie d. techn. Chem., loc cit).

Titanium-containing zeolites are most advantageously used for the novel process. U.S. application Ser. No. 3,329,481 discloses materials in which the Si(IV) in the silicate framework is said to have been replaced with titanium as Ti(IV). These titanium zeolites, in particular those having a crystal structure of the MFI type (cf. Meier and Olson, loc cit), and possibilities for their preparation are described in, for example, U.S.

application Ser. No. 4,410,501, EP-A-311 983, U.S. application Ser. No. 4,666,692, DE-A-30 47 798 or BE-A-10 01 038. Titanium-containing zeolites having different structures are disclosed in EP-A-405 978. In addition to silicon and titanium, such materials may also contain additional elements, such as aluminum (DE-A-31 41 238), gallium (EP-A-266 825), boron (U.S. application Ser. No. 4,666,692) or small amounts of fluorine (EP-A-292 363).

It is known that titanium zeolites having an MFI structure can be identified from a certain X-ray diffraction pattern and additionally from an IR lattice vibration band at about 950 cm$^{-1}$ (DE-A-30 47 798; Snamprogetti) and thus differ from alkali metal titanates or crystalline and amorphous $TiO_2$ phases.

It is known that titanium zeolites having an MFI structure are suitable as catalysts for oxidation reactions (B. Notari, Stud. Surf. Sci. Catal. 37 (1987), 413–425, Amsterdam). For example, in EP-A-110 119 a process is claimed in which propens can be epoxidized in the aqueous phase with hydrogen peroxide over titanium zeolites to give propylene oxide. The preparation of cyclohexanone oxime from cyclohexanone by reaction with ammonia and hydrogen peroxide is described in EP-A-208 311 and the hydroxylation of aromatics is disclosed in GB-A-2 116 974. EP-A-376 453 describes the oxidation of saturated $C_2$-$C_{18}$-hydrocarbons with $H_2O_2$ over the abovementioned titanium zeolites. EP-A-314 147 discloses that aliphatic secondary amines can be oxidized with these catalysts to the corresponding hydroxylamines. This reaction is known from Houben-Weyl, Methoden der organischen Chemie, 4th Edition, Vol. E 16a, pages 178–186 (1990), and does not present the problems encountered in the hydroxylation of azoles.

The titanium silicate zeolites prepared by the processes described can be used for the catalytic conversion of organic molecules. Reactions of this type are known from, inter alia, W. Hölderich, Zeolites: Catalysts for the synthesis of organic compounds, Elsevier, and Stud. Surf. Sci. Catal. 49 (1989), 69–93, Amsterdam, and, for possible oxidation reactions, from Stud. Surf. Sci. Catal. 37 (1987), 413–425.

Typically, the abovementioned titanium zeolites are prepared by reaction of an aqueous mixture of an $SiO_2$ source, a titanium dioxide and a nitrogen-containing organic base, for example tetrapropylammonium hydroxide, with or without the addition of an alkali, in a pressure vessel at elevated temperatures over a period of several hours or a few days, the crystalline product being formed. This is filtered off, washed and dried and is calcined at elevated temperatures to remove the organic nitrogen base. In the resulting powder, some or all of the titanium present within the zeolite framework in varying amounts with four-, five- or six-fold coordination (J. Chem. Soc. Chem. Commun. (1991), 678–680). To improve the catalytic behavior, washing several times with hydrogen peroxide solution containing sulfuric acid can then be effected, after which the titanium zeolite powder must be dried and calcined again, as described in, for example, EP-A-267 362. The titanium zeolite powder can be processed with suitable inert binder in a shaping step in order to make it available as a catalyst in a form which can be more easily handled. A method for this purpose is described in EP-A-200 260.

DE-A-41 38 155 describes a novel process for the crystallization of titanium silicates having a zeolite structure by hydrothermal reaction of an $SiO_2$ source with a titanium component in the presence of aqueous solutions of tetraalkylammonium halides in low concentration and in addition ammonia. This process makes it possible to obtain the resulting titanium zeolite crystals in high yield directly in the form of substantially alkali-free, large lamellar primary crystallites which, owing to their particle size, can be used, without further shaping steps, as catalysts for the conversion of organic molecules, in particular in fluidized bed, trickle-bed or suspension procedures.

It is possible to dispense with the use, described above, of expensive tetrapropylammonium hydroxide if instead small amounts of cheap tetrapropylammonium halides, for example tetrapropylammonium bromide (TPABr), are used and a molar ratio of $TPABr/SiO_2$ of from 0.042:1 to 0.2:1, preferably from 0.042:1 to 0.15:1, is maintained in the reaction mixture. It has proven advantageous to carry out the crystallization of the titanium silicates having a zeolite structure by a hydrothermal method at from 100° to 250° C., in particular from 120° to 200° C., particularly preferably from 150° to 190° C. It is appropriate to maintain a molar ratio of ammonia, used as an aqueous solution, to $SiO_2$ of from 10:1 to 1:1, preferably from 6:1 to 1.5:1, particularly preferably from 5:1 to 3:1.

In this process, titanium silicate zeolites which can be used as catalysts are obtained by adding the titanium component, in the form of a soluble, aqueous or aqueous alcoholic peroxotitanate compound, to the reaction mixture in the hydrothermal reaction in the manner described above. This is achieved by using an $SiO_2/TiO_2$ ratio in the reaction mixture of from 10 to 1500, in particular from 10 to 250, preferably from 10 to 100, and/or containing a dilution of $SiO_2/H_2O$ of from 0.07 to 0.25, preferably from 0.05 to 0.04.

As a result of the alkali-free process, moreover, the material is present in a catalytically active form, without further shaping, after a heat treatment at from 350° to 600° C., preferably from 400° to 550° C., particularly advantageously from 450° to 500° C., directly and without additional ion exchange and in particular because of the crystal size of more than 1 μm and the lamellar crystal shape and can be used as a catalyst.

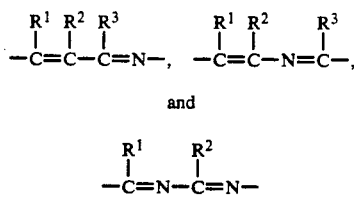

and $R^1$, $R^2$ and R3 are each hydrogen, $C_1$-$C_4$-alkyl, such as methyl, ethyl, n-propyl, isopropyl, n-butyl, isobutyl, sec-butyl or tert-butyl, preferably methyl or ethyl, particularly preferably methyl, or halogen, such as fluorine, chlorine, bromine or iodine, preferably fluorine, chlorine or bromine, particularly preferably fluorine or chlorine.

Examples of starting materials among the azoles II are pyrazole, imidazole, 1,2,4-triazole, 3-chloropyrazole, 3-methylpyrazole, 4-methylpyrazole and 3,5-dimethylpyrazole.

Examples of N-hydroxyazoles I are N-hydroxypyrazole, N-hydroxyimidazole, N-hydroxy-1,2,4-triazole, N-hydroxy-3-chloropyrazole, N-hydroxy-3- methylpyrazole, N-hydroxy-4-methylpyrazole and N-hydroxy-3,5-dimethylpyrazole.

N-Hydroxyazoles I are useful starting materials for the synthesis of compounds having a broad biological action spectrum. For example, EP-A-388 665 describes the preparation of insecticides based on N-hydroxypyrazole and N-hydroxytriazole. Fungicides which can be used in the agricultural sector can likewise be prepared using N-hydroxypyrazole (DE-A-39 05 948) or N-hydroxytriazole (DE-A-39 06 771 and EP-A-421 227). The synthesis of nitrification inhibitors according to DE-A-34 09 317 is likewise carried out using N-hydroxypyrazole.

EXAMPLES

Preparation of the catalyst

Catalyst A 112.5 g of demineralized water are cooled to 5° C. in a glass flask provided with a stirrer and a reflux condenser. 34.7 g of tetraisopropyl orthotitanate and 203.6 g of hydrogen peroxide solution (30% by weight) are added dropwise in the course of 15 minutes. 527.5 g of an ammonia solution (25% by weight) are added to the resulting orange-red solution, and the mixture formed is allowed to warm up to room temperature overnight. Finally, the stirred mixture is heated at 80° C. for 3 hours. Any weight loss is compensated by adding a corresponding amount of ammonia solution. The solution thus prepared is introduced, together with 73.5 g of tetrapropylammoniumbromide, 224.8 g of water and 264.1 g of Ludox AS-40 silica sol, into a steel autoclave having a stirring apparatus.

The reaction mixture is reacted in the course of 168 hours at 185° C. while stirring at 100 rpm and is then cooled, after which the crystalline product is filtered off, washed neutral, dried, and calcined at 500° C. in the air in the course of 5 hours.

The product has the typical X-ray diffraction pattern of the TS-1 titanium silicalite. The crystals have a size of from 2 to 25 $\mu$m and a lamellar habit. The IR spectrum clearly shows a well defined band of 955 cm$^{-1}$. Chemical analysis gives a molar Si/Ti ratio of 16.6 in the product. The yield of crystalline, calcined product is 96.3%, based on the SiO$_2$ used.

Catalyst B 45.2 g of demineralized water are cooled to 5° C. in a glass flask provided with a stirrer and a reflux condenser. 6.9 g of tetraisopropyl orthotitanate and 81.5 g of hydrogen peroxide solution (30% by weight) are added dropwise in the course of 15 minutes. 211.0 g of an ammonia solution (25% by weight) are added to the resulting orange-red solution, and the mixture formed is allowed to warm up to room temperature overnight. Finally, the stirred mixture is heated at 80° C. for 3 hours. Any weight loss is compensated by adding a corresponding amount of ammonia solution. The solution thus prepared is introduced, together with 14.7 g of tetrapropylammonium bromide, 75.5 g of water and 22.1 g of Aerosil 200 (Degussa, pyrogenic silica) into a steel autoclave.

The reaction mixture is reacted in the course of 168 hours at 185° C. and is then cooled, after which the crystalline product is filtered off, washed neutral, dried, and calcined at 500° C. in the air in the course of 5 hours.

The product has the typical X-ray diffraction pattern of the TS-1 titanium silicalite. The crystals have a uniform size of about 8 $\mu$m with a lamellar habit. The IR spectrum of the sample clearly shows a well defined band of 960 cm$^{-1}$. Chemical analysis gives a molar Si/Ti ratio of 37.7 in the product. Contaminations by alkali metal are only 0.0015% by weight of sodium and 0.0045% by weight of potassium. The yield of crystalline, calcined product is 90.3%, based on SiO$_2$ used.

Examples 1 to 25

The reactions were carried out in a glass autoclave having a magnetic stirrer (from 250 to 1,000 ml) in the liquid phase. The specific procedure was as follows: 10 g of azole were dissolved in 30 ml of isopropanol, and the amounts of solid catalyst stated in Tables 1 and 2 were added. Heating was then carried out to the stated temperature, after which the corresponding amount of an aqueous hydrogen peroxide solution was added dropwise. The reaction mixture was stirred further until peroxide was no longer detectable (Merck test rod). Thereafter, a further 30 ml of solvent were added all at once, the mixture was cooled and the catalyst was then filtered off. The reaction solution was analyzed in a known manner by calibrated HPLC. Conversions and selectivities are likewise shown in Tables 1 and 2.

TABLE 1

Hydroxylation of pyrazole

| Experiment No. | Catalyst | Azole/Cat. ratio [g/g] | H$_2$O$_2$/Azole ratio [mol/mol] | Temp. [°C.] | Time [h] | Conversion [wt. %] | Select. [mol %] |
|---|---|---|---|---|---|---|---|
| 01 | A | 3.3 | 0.5 | 80 | 4.25 | 36.2 | 44.2 |
| 02 | A | 3.3 | 1.0 | 80 | 3.75 | 45.2 | 49.3 |
| 03 | A | 3.3 | 2.5 | 80 | 3.75 | 66.3 | 48.4 |
| 04 | B | 3.3 | 1.0 | 80 | 4.25 | 48.6 | 37.9 |
| 05 | B | 3.3 | 2.5 | 80 | 3.75 | 49.3 | 29.4 |
| 06 | A | 3.3 | 2.5 | 80 | 15.75 | 57.9 | 35.2 |
| 07 | A | 3.3 | 2.5 | 80 | 5.25 | 72.3 | 40.5 |
| 08 | A | 1.7 | 2.5 | 80 | 3.25 | 57.5 | 31.2 |
| 09 | A | 3.3 | 1.0 | 60 | 4.25 | 65.6 | 28.0 |
| 10 | B | 1.0 | 1.0 | 60 | 4.25 | 72.0 | 23.8 |
| 11 | B | 1.0 | 2.0 | 80 | 4.50 | 67.7 | 44.0 |
| 12 | B | 1.0 | 3.0 | 80 | 4.50 | 71.5 | 43.7 |
| 13 | A | 1.0 | 3.0 | 80 | 4.25 | 77.0 | 22.8 |
| 14 | B | 1.0 | 2.0 | 60 | 4.25 | 73.5 | 46.5 |
| 15 | A | 1.0 | 2.0 | 60 | 4.25 | 65.6 | 40.9 |
| 16 | A | 3.3 | 1.0 | 80 | 5.00 | 27.1 | 66.1 |
| 17 | B | 3.3 | 1.0 | 60 | 5.00 | 23.6 | 67.9 |
| 18 | A | 3.3 | 1.0 | 60 | 5.00 | 28.0 | 73.5 |

TABLE 1-continued

| | | Hydroxylation of pyrazole | | | | | |
|---|---|---|---|---|---|---|---|
| Experiment No. | Catalyst | Azole/Cat. ratio [g/g] | H₂O₂/Azole ratio [mol/mol] | Temp. [°C] | Time [h] | Conversion [wt. %] | Select. [mol %] |
| 19 | A | 3.3 | 2.5 | 60 | 5.00 | 33.7 | 52.1 |

TABLE 2

| | | Hydroxylation of pyrazole | | | | | |
|---|---|---|---|---|---|---|---|
| Experiment No. | Catalyst | Azole/Cat. ratio [g/g] | H₂O₂/Azole ratio [mol/mol] | Temp. [°C] | Time [h] | Conversion [wt. %] | Select. [mol %] |
| 20 | A | 3.3 | 0.5 | 80 | 3.75 | 20.9 | 40.5 |
| 21 | B | 3.3 | 0.5 | 80 | 3.75 | 20.5 | 34.0 |
| 22 | A | 3.3 | 1.0 | 80 | 3.75 | 35.2 | 35.5 |
| 23 | B | 3.3 | 2.5 | 80 | 3.75 | 58.5 | 33.0 |
| 24 | A | 3.3 | 1.0 | 80 | 3.75 | 28.9 | 37.7 |
| 25 | A | 3.3 | 2.5 | 80 | 3.75 | 48.3 | 30.8 |

We claim:

1. A process for the preparation of an N-hydroxyazole of the formula I

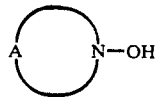 (I)

where A is

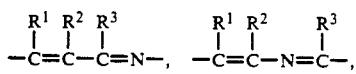

and

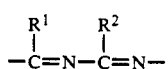

and $R^1$, $R^2$ and $R^3$ are each hydrogen, $C_1$-$C_4$-alkyl or halogen, wherein an azole of the formula II

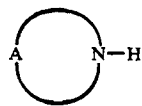 (II)

where A, $R^1$, $R^2$ and $R^3$ have the abovementioned meanings, is reacted with hydrogen peroxide or an alkyl peroxide in the presence of a zeolite catalyst at from $-20°$ to $150°$ C. and from 0.1 to 150 bar.

2. A process for the preparation of an N-hydroxyazole I as claimed in claim 1, wherein the reaction is carried out over a zeolite catalyst of the pentasil type.

3. A process for the preparation of an N-hydroxyazole I as claimed in claim 1, wherein the zeolite catalyst used is a titanium zeolite.

4. A process for the preparation of an N-hydroxyazole I as claimed in claim 1, wherein the reaction is carried out at from $0°$ to $120°$ C.

5. A process for the preparation of an N-hydroxyazole I as claimed in claim 1, wherein the reaction is carried out at from 0.5 to 80 bar.

* * * * *